US009146202B2

(12) United States Patent
Partington et al.

(10) Patent No.: US 9,146,202 B2
(45) Date of Patent: Sep. 29, 2015

(54) NEUTRON BACKSCATTER INSTRUMENT

(75) Inventors: Thomas John Partington, Leeds (GB); Peter Jackson, London (GB); Ken Pearson, legal representative, Subiaco (AU)

(73) Assignee: JOHNSON MATTHEY PUBLIC LIMITED COMPANY, London (GB)

( * ) Notice: Subject to any disclaimer, the term of this patent is extended or adjusted under 35 U.S.C. 154(b) by 0 days.

(21) Appl. No.: 13/978,595

(22) PCT Filed: Jan. 5, 2012

(86) PCT No.: PCT/GB2012/050009
§ 371 (c)(1),
(2), (4) Date: Feb. 18, 2014

(87) PCT Pub. No.: WO2012/093256
PCT Pub. Date: Jul. 12, 2012

(65) Prior Publication Data
US 2014/0191135 A1 Jul. 10, 2014

(30) Foreign Application Priority Data
Jan. 6, 2011 (GB) .................................. 1100160.9

(51) Int. Cl.
G01N 23/204 (2006.01)
G01F 23/288 (2006.01)

(52) U.S. Cl.
CPC ............ *G01N 23/204* (2013.01); *G01F 23/288* (2013.01)

(58) Field of Classification Search
CPC .................................................. G01N 23/204
USPC ............................................ 250/391, 390.01
See application file for complete search history.

(56) References Cited

U.S. PATENT DOCUMENTS

| 3,716,711 | A |  | 2/1973 | Olesen |  |
|---|---|---|---|---|---|
| 4,243,886 | A |  | 1/1981 | Untermyer, II |  |
| 4,918,315 | A | * | 4/1990 | Gomberg et al. | ........ 250/390.04 |
| 7,569,810 | B1 | * | 8/2009 | Troxler et al. | ............ 250/269.1 |
| 2006/0022636 | A1 |  | 2/2006 | Xian et al. |  |

FOREIGN PATENT DOCUMENTS

| EP | 1 732 085 A1 | 12/2006 |
|---|---|---|
| JP | 2007163352 A | 6/2007 |
| WO | 93/12407 A1 | 6/1993 |

OTHER PUBLICATIONS

GB Search Report, dated Mar. 24, 2011, from corresponding GB application.
International Search Report, dated Sep. 12, 2012, from corresponding PCT application.

* cited by examiner

Primary Examiner — David Porta
Assistant Examiner — Faye Boosalis
(74) Attorney, Agent, or Firm — Young & Thompson

(57) ABSTRACT

Disclosed is an instrument for detecting neutron backscatter from an object including a source of neutrons (12), a neutron detector (14) capable of detecting thermal neutrons and a housing (10) which is impervious to water and having at least one external operating surface (20) for placing adjacent the object, the source and detector being located within the housing in such a way that the distance between the detector and the operating surface(s) is less than 25 mm and the distance between the detector and any other external surface of the housing is at least 50 mm.

20 Claims, 2 Drawing Sheets

NEUTRON BACKSCATTER INSTRUMENT

BACKGROUND OF THE INVENTION

1. Field of the Invention

The present invention concerns a neutron backscatter instrument for detecting and identifying the contents of a vessel. The instrument is especially adapted for use in water, i.e. for sub-sea measurements but may be useful in other environments.

2. Description of the Related Art

It is frequently a requirement to identify and estimate the level of fluids (including vapour and liquids) such as water or hydrocarbon fuels in vessels located underwater. For example, it may be necessary to measure the amount of water in a buoyancy tank. Another important application for sub-sea measurement is in the salvage of submerged or sunken sea-going marine vessels or wrecks, in order to locate fuels for recovery and to avoid leakage into the environment as the vessel structure degrades over time. It may be required to recover fuel, for example, as part of an environmental protection scheme or maritime emergency response. Neutron backscatter measurement involves emitting fast neutrons from a neutron generator into a material, then detecting and measuring the number and/or energy of the thermal neutrons scattered from the material as a result of interaction of the molecules of the material with the fast neutrons in order to provide information about an object, including the contents of a vessel. One problem with using neutron backscatter measurements in a hydrogen-rich environment, for example underwater, is that most neutron detectors are very sensitive to thermal neutrons scattered from hydrogen-rich materials such as water. Therefore the sensitivity of the detector to other materials is reduced because of the large number of counts received from the water. It is an object of the invention to overcome at least some of the problems associated with using neutron backscatter instruments in an underwater environment.

U.S. Pat. No. 3,716,711 describes a water-level gauge, using a neutron source, for indicating the water-level in a sunken vessel. The device is designed to be placed against the flat external wall of a vessel so that neutrons emitted from the source can enter the vessel and interact with its contents. Slow neutrons which are scattered by water present within the vessel are then detected by the detector within the water-level gauge. The gauge incorporates a moulded urethane shroud to provide buoyancy.

BRIEF SUMMARY OF THE INVENTION

According to the invention an instrument for detecting neutron backscatter from an object comprises a source of neutrons, a neutron detector capable of detecting thermal neutrons and a housing which is impervious to water and having at least one external operating surface for placing adjacent said object, said source and detector being located within the housing in such a way that the distance between the detector and any other external surface except the operating surface of the housing is at least 50 mm. Preferably the distance between the detector and any other external surface of the housing is at least 75 mm-100 mm, especially about 150 mm. The housing does not contain water or any hydrogen-rich material such as polymeric materials for buoyancy. The presence of hydrogen-containing material within the housing is minimised. The housing is essentially free of hydrogen-containing material, which, in the context of this invention means that water, hydrocarbon or polymeric material is not present, save for a minimal amount of such material present in the components of the instrument, such as might be found in cables or electronics components. This ensures that the detection of neutrons scattered by such hydrogen-rich material is minimised. The operating surface may be generally flat or alternatively may be profiled to fit against the surface of the object which is to be scanned. For example, the operating surface may be curved, especially arcuate, when the instrument is intended for scanning cylindrical objects such as pipelines. In a preferred embodiment the instrument is provided with one or more "shoes" or coupling plates for mounting against the operating surface of the instrument, each coupling plate having a surface to bear against the operating surface of the instrument and an operating surface adapted to fit against the object to be scanned. In this embodiment the instrument operating surface (and also the surface of the (or each) coupling plate which is adapted to bear against the operating surface of the instrument) is preferably flat. The operating surface of the coupling plate is preferably shaped or profiled to fit against the surface of the object to be scanned. The coupling plate and housing are provided with means to mount and demount the coupling plate to/from the instrument. By providing an instrument or a coupling plate having a profiled operating surface which is adapted to fit against the surface of the object to be scanned, the presence of water between the operating surface of the instrument and the object may be minimised.

The operating surface of the instrument and/or of a coupling plate may include alternative or additional means to exclude water from the space between the operating surface and the object. Such means may include a skirt for bounding a space from which water may be removed. The skirt, if present, may be formed from a material containing few hydrogen atoms, such as neoprene rubber, for example. The operating surface of the instrument, shoe/coupling plate or a surface of the object may be provided with a layer of a gel or other deformable material so that the operating surface and the object may be brought into close proximity and water may be excluded from the space therebetween. It is frequently sufficient to bring the operating surface of the instrument and the object close together in order for sufficient water to be excluded from the space between the object and the instrument without providing additional water-excluding means.

The housing is made from a material which is suitably tough to withstand the conditions, e.g. pressure, temperature, in the intended operating environment. The housing material should be relatively transparent to thermal neutrons, i.e. it should have a relatively low neutron cross-section so that a high proportion of the thermal neutrons scattered from the object can pass through the housing to be detected by the detector. The housing is preferably formed from metal. For certain applications, such as sub-sea operation, the instrument, and therefore the housing, is preferably relatively light in weight so that it can be easily manoeuvred by a diver or ROV when required. Aluminium and titanium are preferred materials for such applications, although certain types of steel may be suitable for some purposes. The housing may be in the form of a shell enclosing a space within which the source and detector are located. In this form the space may be wholly or partially filled with a fluid such as a silicone oil. Alternatively the space between the walls of the housing and the detector may be wholly or partially filled with a metal in solid form or as a foam. In such a case, the housing may be formed from a block of metal having spaces formed within it to receive the source and detector. The block may include voids in order to reduce the weight of the instrument although its peripheral walls should be watertight, as noted above. The housing may be formed in any suitable shape. For underwater, especially sub-sea, use the housing is preferably formed in a shape which can withstand external pressure and therefore, curved, cylindrical or dome-shaped housings are preferred, although the operating surface of the housing is usually generally flat. The housing may be marked with an indicator to show the position of the source. The housing may incorporate a visual display in order to indicate the status of the instrument or the counts detected by the detector.

The neutron source is selected from suitable available neutron sources such as neutron generators and radioisotope sources. The selection of an appropriate neutron source should be made according to the situation and application for which the method is applied. The preferred type of neutron source is an isotope source such as californium ($^{252}$Cf) or americium/beryllium ($^{241}$Am/Be) which tends to be cheaper and has a longer half-life.

The neutron detector is capable of detecting slow (thermal) neutrons. One preferred type of detector comprises a proportional counter which is filled with $^3$He gas. This detector is virtually unaffected by the fast neutrons emitted from the source, and this feature allows the source and detector to be located adjacent to each other. Other neutron detectors such as those comprising boron, either as a coating or in the form of $BF_3$ gas, or a suitable form of scintillation detector may also be used. The purpose of the detector is to count slow neutrons so that the presence or absence of a hydrogen-rich fluid, such as a hydrocarbon fuel for example, may be determined. Depending on the type of detector used, it may be possible also to detect and record the energy of each thermal neutron detected. The energy of the detected neutrons can provide information about the degree of thermalisation of the scattered neutrons which may be interpreted to provide information about the identity of the material(s) through which the neutron has passed. In use, the instrument is held in place against the object so that the source emits neutrons into the object and the detector detects neutrons from the object for a suitable period of time, which is typically at least 1 second and normally less than 5 minutes. In some applications sufficient information may be gathered from detection time of less than a second.

The source and detector are located within the housing in such a way that the distance between the detector and the operating surface(s) is preferably less than 50 mm, more preferably not more than 25 mm. By minimising the distance between the operating surface and the detector, the chance of detecting thermal neutrons scattered from the vessel through the operating surface of the housing is increased. Preferably the distance between the source and the operating surface(s) is small, e.g. less than about 25 mm in order to maximise the number of fast neutrons emitted from the source that enter the object through the operating surface. As noted above, when the neutron detector is relatively insensitive to fast neutrons, the detector and source may be placed close together. In one preferred embodiment of the instrument, the source is placed approximately centrally relative to the detector. The detector may be shielded from the source by a material having a high neutron cross-section, such as cadmium or gadolinium or a material containing boron, e.g. in the form of a sheet between 1 and about 25 mm thick. The shielding may extend to shield the detector from neutrons from other directions except neutrons received at, or passing through, the operating surface of the housing. The shielding may be placed around the detector, in close proximity thereto. The shielding may, in some embodiments, wholly or partially surround the housing, and may form a part of the external wall of the housing. Alternatively the shielding material may form a layer within the external wall of the housing. The shielding material is not placed in such a position as to shield the detector from neutrons passing through the operating surface of the instrument.

The instrument preferably includes handling means for handling and maneuvering the housing so that it can be placed in the required position for acquiring information from an object. For underwater use the handling means are suitable for use by a diver or a remotely-operated vehicle (ROV) as typically used in sub-sea exploration, operations and salvage. The handling means may therefore include standard or specifically designed couplings to interface with commercially-available ROVs. The handling means may incorporate operating means such as a switch so that the instrument may be operated by a diver or ROV.

In a preferred form of the invention the instrument is provided with means for mounting the instrument on and preferably also demounting it from a support. The support may take the form of a framework. The support is provided with handling means and optionally operating means and serves to facilitate maneuvering of the instrument relative to the object to be measured. Alternatively, such handling and operating means may be provided on the instrument itself. In a preferred form, the support incorporates means for stabilising the instrument in a particular position relative to the object so that it can be held approximately stationary whilst a neutron backscatter measurement is made. Preferably the support is capable of temporarily attaching to the object whilst a measurement is taken. Suction cups are convenient for providing the required temporary attachment, particularly for use underwater. Magnetic clamps may provide a suitable alternative. When such temporary attachment means are provided, suitable operating means are present for attaching and releasing the support or instrument from the object to be measured. A shoe and/or skirt, as described above, to adapt the operating surface to the shape of the object to be measured, may be provided on the support. Alternatively, means for attaching the instrument to an object during measurement may be provided directly on the instrument. The instrument is provided with a suitable power supply. The power supply may comprise a battery or batteries located within the housing. The battery may be rechargeable. Alternatively, or as an additional feature, the instrument may be powered by means of a power supply located in a unit outside the housing, for example in an ROV unit, connected to the instrument by means of a cable.

The housing contains suitable electronics components and circuitry to power the detector and generate a signal representing the number of neutrons detected by the detector. The electronics may comprise one or more power converters, a high voltage generator, signal processing apparatus, amplifiers, discriminators, filters and means for reducing signal noise. In a preferred embodiment, negative going pulses are provided on the incoming power supply as an output.

Data from the detector recording the number of counts detected over a particular time interval may be stored within a data-logger within the housing, or it may be transmitted to a remote data receiver and data processor either wirelessly or by means of a cable. In such a case, the data receiver may be located with an operator such as a diver, ROV instrument or a controller located at the surface, e.g. on a ship. In a preferred embodiment, a signal, incorporating information concerning the number of neutrons within a predetermined range of energies which have been detected by the detector, is transmitted from the instrument to a remote unit containing a data-processor. The remote unit may then carry out data analysis to provide information about the object scanned with the instrument. The remote unit may re-transmit the signal received from the instrument to a different unit or it may interpret the signal and display information derived from the signal to the user. The number of counts, and, where appropriate, their energies, detected by the detector may be interpreted to provide the required information about the object which is scanned. The backscatter count rate is largely dependent on the hydrogen concentration per unit volume in the scattering material and so the backscatter count rate may be used to provide information relating to the identity of the material and/or the identification of an interface between materials by identification of a change in the count rate between different parts of the scanned object. In the case of a vessel in which the presence of a hydrocarbon fuel is likely, the use of the instrument may therefore be capable of confirming the presence of a hydrogen-rich material, providing information useful in identifying the material as water or a hydrocarbon fuel and identifying the level of such fluids in the vessel.

BRIEF DESCRIPTION OF THE DRAWINGS

An example of the invention will now be described with reference to the accompanying drawings.

DETAILED DESCRIPTION OF THE PREFERRED EMBODIMENTS

Figure 1:
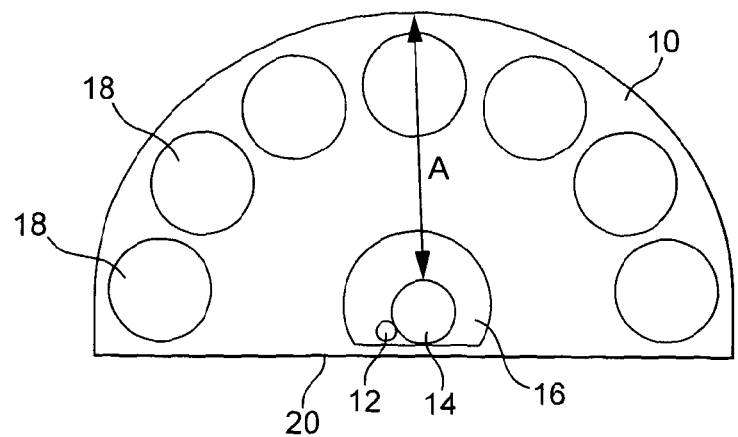
FIG. 1: a view through a transverse section of the instrument.
Figure 2A:
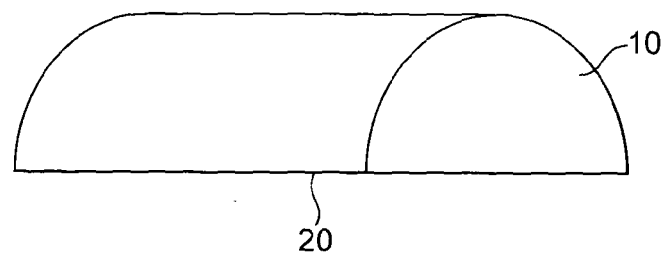
FIGS. 2A & 2B: perspective views of the instrument.
Figure 2B:
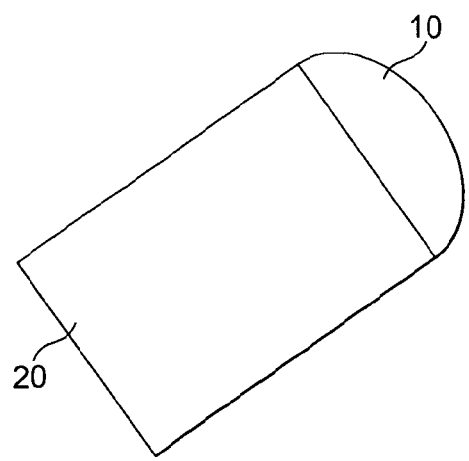

FIG. 1 shows a view through a transverse section of the instrument. A housing 10 is formed from aluminium. A neutron source 12 and slow-neutron detector 14 are located in a channel 16 extending through the housing close to the operating surface 20. Channels 18, extending through the housing, are present to reduce the weight of the instrument. Line A represents the distance between the detector and the external wall of the housing which is not the operating surface. This distance is approximately 150 mm in the embodiment shown. FIG. 2 shows alternative sketch perspective views of the instrument. The housing may contain a current-limited 9V to 24V DC power supply output signal by which means the incoming signal is filtered and protected and then regulated down to 5V DC to power all stages. The detector is a $He^3$ tube powered by a high voltage generator. The signal from the detector, in the form of low level pulse fed via a high voltage capacitor to be processed by a preamplifier and then fed to a discriminator in which they are coupled to a comparator to discriminate the pulses from low-level noise. The output of the comparator triggers a monostable circuit that drives pulses to the power supply stage via a field effect transistor.

Figure 3:
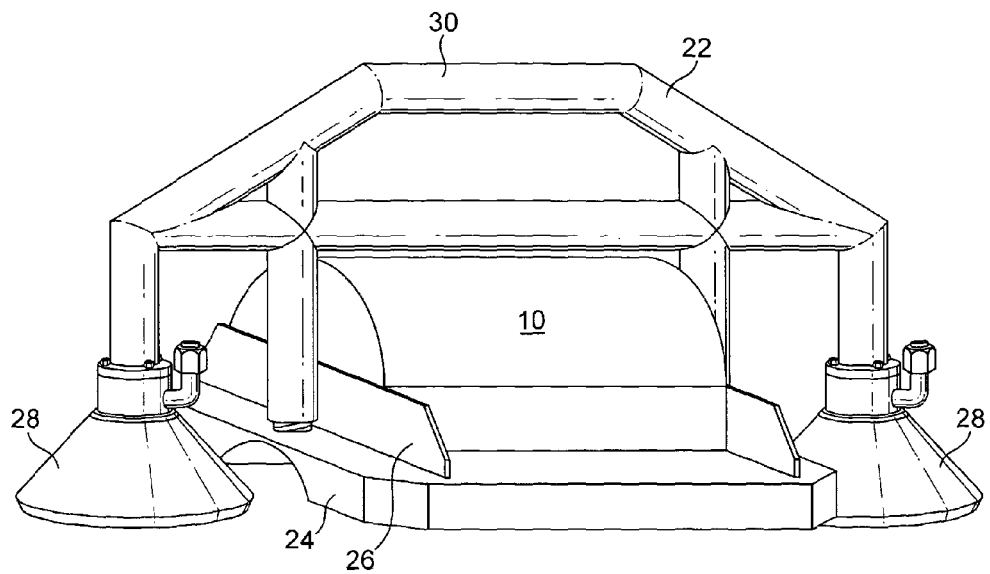
FIG. 3: a perspective view of the instrument within a support frame.
Figure 4:
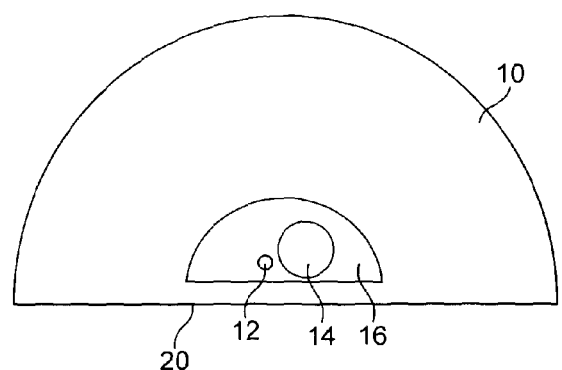
FIG. 4: a view through a transverse section of and alternative embodiment of the instrument.

In FIG. 3, the instrument is shown within a support frame 22. The support includes a handle portion 30 and a cradle portion 26 for receiving the instrument. A shoe 24 is provided beneath the cradle which abuts the operating surface of the instrument. The shoe is designed to fit around a portion of a cylindrical object and is useful for scanning objects such as pipelines using the instrument. Suction cups 28 are operable to secure the support, and the instrument within it, to an object to be scanned. FIG. 4 shows an alternative embodiment of the instrument which is similar to the embodiment of FIG. 1, except that it does not include the channels 18.

The invention claimed is:

1. An instrument for detecting neutron backscatter from an object comprising a source of neutrons, a neutron detector capable of detecting thermal neutrons and a housing which is impervious to water and having at least one external operating surface for placing adjacent said object, said source and detector being located within the housing in such a way that the distance between the detector and any external surface of the housing except the operating surface is at least 50 mm, wherein said housing is essentially free of hydrogen-containing material and wherein a space between walls of the housing and the detector is wholly or partially filled with a metal in solid form or as a foam.

2. An instrument according to claim 1, wherein the housing is formed from a block of metal having spaces formed therein that receive the source and the detector.

3. An instrument according to claim 2, wherein the block further includes voids.

4. An instrument according to claim 1, wherein the distance between the detector and any external surface of the housing except the operating surface is at least 100 mm.

5. An instrument according to claim 1, wherein the distance between the detector and the operating surface is less than 50 mm.

6. An instrument according to claim 1, wherein the operating surface is generally flat.

7. An instrument according to claim 1, wherein the operating surface is profiled to fit against the surface of the object which is to be scanned.

8. An instrument according to claim 1, further comprising at least one coupling plate adapted for mounting against the operating surface, each coupling plate having a surface to bear against the operating surface of the instrument, an operating surface adapted to fit against the object to be scanned and means to mount and demount the coupling plate to/from the instrument.

9. An instrument according to claim 1, wherein at least one external surface of the housing is curved, cylindrical or dome-shaped.

10. An instrument according to claim 1, wherein the housing incorporates a visual display.

11. An instrument according to claim 1, wherein the neutron source comprises a radioisotope source.

12. An instrument according to claim 1, wherein a neutron-absorbing material is positioned to shield the detector from neutrons except neutrons passing through the operating surface of the housing.

13. An instrument according to claim 1, further comprising a support and means for mounting on and demounting the instrument from a support, said support being provided with handling means.

14. An instrument according to claim 1, further comprising wireless or wired transmission means to transmit data from the detector to a remote data receiver and data processor.

15. A method of gathering information about an object comprising the steps of performing a neutron backscatter measurement using an instrument and using the number of thermal neutrons counted by the detector to provide the required information about the object, wherein said instrument is an instrument for detecting neutron backscatter from an object and comprises
   a. a source of neutrons,
   b. a neutron detector capable of detecting thermal neutrons, and
   c. a housing which is impervious to water, is essentially free of hydrogen-containing material and having at least one external operating surface for placing adjacent said object, wherein a space between walls of the housing and the detector is wholly or partially filled with a metal in solid form or as a foam, and wherein said source and detector are located within the housing in such a way that the distance between the detector and any external surface of the housing except the operating surface is at least 50 mm.

16. A method according to claim 15, wherein the housing is formed from a block of metal having spaces formed therein that receive the source and the detector, and wherein the block further includes voids.

17. A method according to claim 15, wherein said object is a vessel located underwater and the required information relates to the identity of material contained within said vessel, and wherein the energies of the thermal neutrons counted by the detector are used to provide the required information about the object.

18. A method according to claim 15, wherein the distance between the detector and any external surface of the housing except the operating surface is at least 100 mm.

19. A method according to claim 15, wherein said instrument further comprises at least one demountable coupling plate adapted for mounting against the operating surface, each coupling plate having a surface to bear against the operating surface of the instrument, and an operating surface adapted to fit against the object to be scanned; and mounting said coupling plate to the instrument.

20. A method according to claim 15, wherein said instrument further comprises a demountable support which is provided with handling means, and wherein said instrument is mounted on said support, and further comprising temporarily attaching said instrument to the object whilst a measurement is taken, and transmitting data from the detector to a remote data receiver by wireless or wired transmission means.

* * * * *